United States Patent [19]

Chamness

[11] 4,256,113
[45] Mar. 17, 1981

[54] SURGICAL APPARATUS

[76] Inventor: Dale L. Chamness, 621 Pleasant Ridge Rd., Bloomington, Ind. 47401

[21] Appl. No.: 858,712

[22] Filed: Dec. 8, 1977

[51] Int. Cl.³ ............................................. A61B 17/36
[52] U.S. Cl. ............................ 128/303.14; 128/303 R; 128/309
[58] Field of Search ........... 128/303 R, 303.1, 303.12, 128/303.13, 303.14, 303.15, 303.16, 303.17, 303.18, 319, 320, 306, 307, 308, 4, 5, 6, 7, 8, 9, 309

[56] References Cited

U.S. PATENT DOCUMENTS

| 1,971,024 | 8/1934 | Wappler | 128/303.15 |
| 2,448,741 | 9/1948 | Scott et al. | 128/303.15 |
| 2,484,059 | 10/1949 | Wallace | 128/303.15 |
| 3,081,767 | 3/1963 | Hett | 128/6 |
| 3,149,633 | 9/1964 | Zingale | 128/303.15 |
| 3,552,384 | 1/1971 | Pierie et al. | 128/303 X |
| 3,955,578 | 5/1976 | Chamness et al. | 128/303.15 |

FOREIGN PATENT DOCUMENTS

| 1250052 | 9/1967 | Fed. Rep. of Germany | 128/7 |
| 192928 | 9/1937 | Switzerland | 128/320 |

*Primary Examiner*—Edgar S. Burr
*Assistant Examiner*—James R. Feyrer
*Attorney, Agent, or Firm*—Jenkins, Coffey, Hyland, Badger & Conard

[57] ABSTRACT

A surgical cannula includes a sheath having proximal and distal ends, a member disposed within the sheath and movable longitudinally therein, the movable member having proximal and distal ends, and a surgical instrument operable by movement of the distal end of the movable member with respect to the distal end of the sheath. The cannula further includes an operating assembly comprising a body or handle which slidably receives a slide for movement longitudinally of the body. The body defines a generally cylindrical interior and the slide includes a pair of longitudinally spaced apart walls having the same general shape as the cross section of the cylinder. The walls are provided with aligned apertures which rotatably receive a stem. The stem includes proximal and distal ends, and the proximal end of the movable member is fixedly attached to the distal end of the stem. The proximal end of the sheath is fixedly attached to the body portion of the handle. The stem is provided with a thumbwheel which is accessible through the side wall of the body, the thumbwheel being manipulatable to rotate the movable member in the sheath. The slide includes a rack, and the body supports an additional thumbwheel having pinion gear teeth formed thereon, the pinion gear teeth engaging the rack. Manipulation of the second-mentioned thumbwheel causes the slide to move longitudinally within the body to move the movable member longitudinally within the sheath.

22 Claims, 6 Drawing Figures

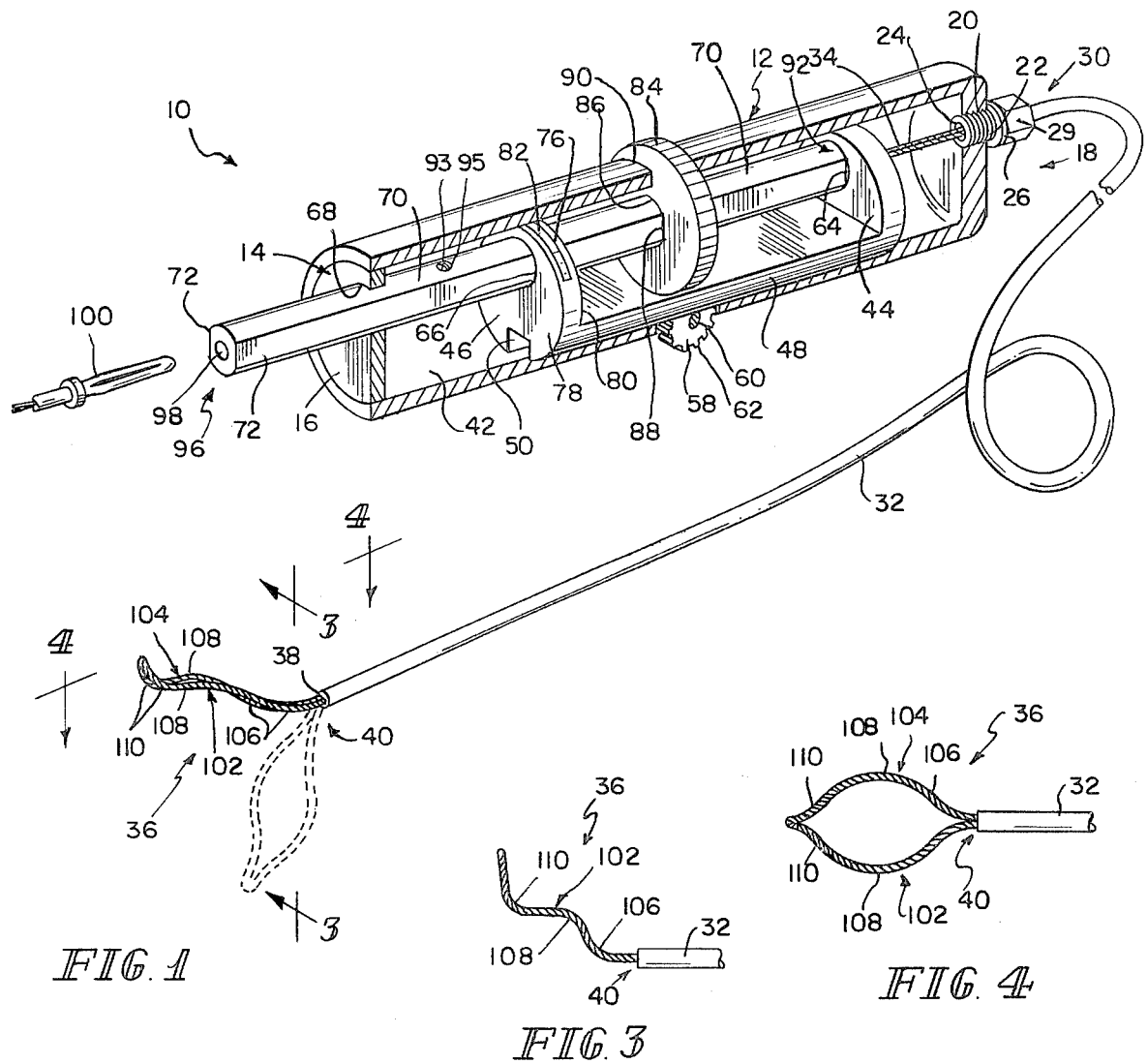
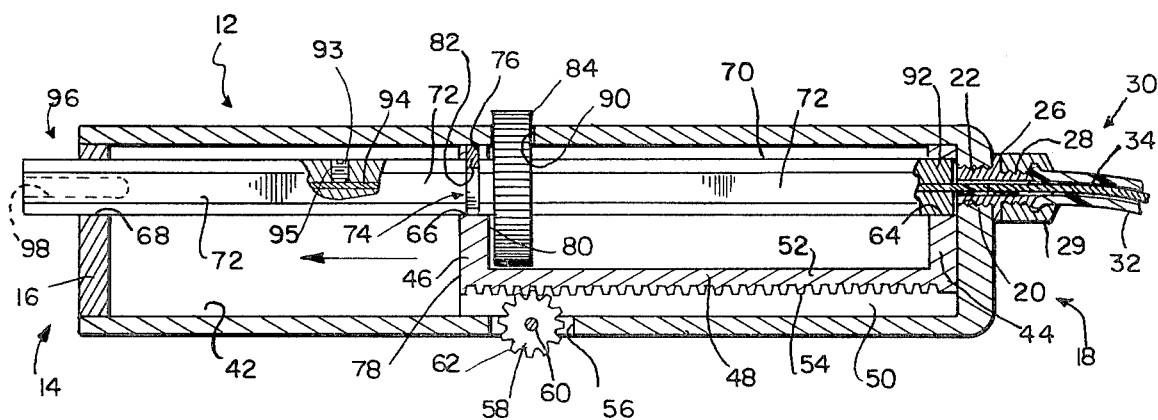

SURGICAL APPARATUS

This invention relates to surgical instruments generally, and more particularly to a surgical snare manipulation apparatus useful for operating polypectomy apparatus, polyp and foreign body retrieval apparatus, cytology brush apparatus, and similar apparatus.

Surgical snares suitable for use in removing polyps, such as those found in the gastrointestinal tract, have been in use for many years. A surgical snare generally includes an elongated flexible sheath connected at its proximal end to an operating handle. Extending through the sheath is an elongated flexible cable, the proximal end portion of which is connected to a movable portion of the operating handle so that the cable can be retracted and protracted by the surgeon relative to the sheath. An operating loop is connected to the distal end portion of the cable which is opened and closed by the surgeon to the extent that he shifts the movable portion of the operating handle to protract or retract the cable. When the cable is in its protracted or forward position, the operating loop is outside the sheath and in its fully extended position. As the cable is retracted, the loop is drawn into the sheath and closed.

Prior art surgical snares have generally suffered from common deficiencies such as ease of manipulation of the operating loop at the point of application, for example, within the gastrointestinal tract of a surgical patient. As can be appreciated, during periods of use, a surgical snare must be manipulated and operated with considerable precision and control.

In addition, many prior art snare handles for use with the available surgical snares are designed so that in order to engage the polyp, it is necessary to rotate the entire handle in order to rotate the operating loop. The operating loop handle usually is connected by an electrical conductor to an RF generator. The conductor has a tendency to become wrapped around the surgeon's hand as he rotates the handle to engage the polyp. Other prior art snares require two-handed operation to rotate and protract or retract the snare simultaneously. This is disadvantageous in that the surgeon may be trying to operate one or more other instruments at the same time he is operating the snare. Prior art structures are found in Chamness et al, U.S. Pat. No. 3,955,578 and references cited therein.

According to the present invention, an apparatus is provided for use with a polypectomy instrument, polyp or foreign body retrieval instrument, cytology brush instrument, or other similar instruments. The apparatus includes a sheath having proximal and distal ends, and a member disposed within the sheath and movable longitudinally therein, the movable member having proximal and distal ends, and a surgical instrument operable by movement of the distal end of the movable member with respect to the distal end of the sheath. The inventive apparatus, an operating assembly for the instrument, comprises first means for moving the movable member longitudinally with respect to the sheath, second means for rotating the movable member within the sheath, and a body for supporting the first and second means, the body including a distal end for fixed attachment of the proximal end of the sheath thereto, the distal end of the body further defining an aperture through which the proximal end of the movable member extends, the proximal end of the movable member being coupled to the first and second means for movement thereby.

In an illustrative embodiment, the first means includes a slide supported in the body for movement longitudinally thereof, the body including means defining a generally cylindrical interior wall and the slide including means providing a pair of walls spaced apart longitudinally of the cylinder axis and shaped to slide in the cylinder, the walls having substantially the same shape as a cross section of the body interior wall. The slide further comprises a portion defining a rack and the body includes a first thumbwheel, the periphery of which provides pinion gear teeth to engage the rack. Manipulation of the first thumbwheel causes movement of the slide longitudinally within the body, and corresponding protraction and retraction of the distal end of the movable member with respect to the distal end of the sheath to operate the surgical instrument.

Further according to the illustrative embodiment, the second means comprises a stem rotatably mounted with respect to the first means by being received in aligned apertures in the longitudinally spaced apart walls of the slide. The stem has proximal and distal ends, the proximal end of the movable member being fixedly attached to the distal end of the stem. The stem includes a second thumbwheel for manipulation to rotate the stem with respect to the first means, the second thumbwheel being accessible through the body. The proximal end of the stem includes means defining a terminal for attachment to a source of electrical energy and a conductor providing electrical contact between the terminal and the proximal end of the movable member. The movable member includes electrically conductive means to supply electricity to the surgical instrument.

Further according to the instant invention, a surgical cannula includes a sheath and a snare extending within the sheath and having proximal and distal ends, a loop formed at the distal end of the snare, and means for protracting the distal end of the snare including the loop from, and retracting the distal end of the snare including the loop into, the distal end of the sheath, the loop being formed with a double offset bend in a plane extending longitudinally of the cannula across the loop, such that partial retraction of the loop into the distal end of the sheath causes the loop to move parallel to the first-mentioned plane and perpendicular to a second plane which is perpendicular to the first-mentioned plane and parallel to the longitudinal extent of the cannula. In the illustrative embodiment, the loop is somewhat W-shaped in the first-mentioned plane, such that partial retraction of the loop into the sheath causes the portion of the loop remote from the sheath to move parallel to the first-mentioned plane and perpendicular to the second-mentioned plane.

The invention may best be understood by referring to the following description and accompanying drawings which illustrate the invention. In the drawings:

FIG. 1 is a partly sectional fragmentary isometric view of an apparatus constructed according to the present invention;

FIG. 2 is a vertical sectional side elevational view of a portion of the apparatus of FIG. 1;

FIG. 3 is a fragmentary sectional view of the surgical snare loop of the apparatus of FIG. 1, taken generally along section lines 3—3 thereof;

FIG. 4 is a fragmentary sectional view of the surgical snare loop of the apparatus of FIG. 1, taken generally along section lines 4—4 thereof;

Figure 5:
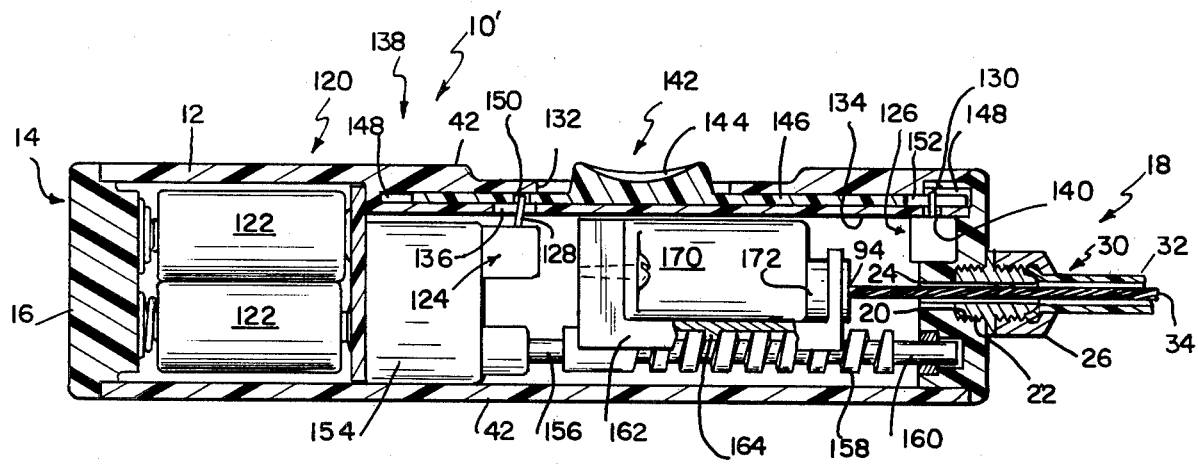
FIG. 5 is a sectional side elevational view of another apparatus constructed according to the present invention; and, FIG. 6 is a partly block and partly schematic diagram showing the wiring of the electrical system of the embodiment of FIGS. 5–6.

The apparatus 10 of the instant invention includes a cannula operating handle or body 12 having a proximal end 14, covered by an end cap 16 and a distal end 18. Distal end 18 includes a threaded aperture 20 which receives a nut 22, also having an aperture 24 extending longitudinally therethrough. Nut 22 is provided with a collar 26 and a forwardly extending portion 28 having outside threads for threadedly engaging a nut 29 (FIG. 2).

The flared proximal end 30 of a cannula sheath 32 is urged onto portion 28 and held in place by tightening nut 29 on threaded portion 28. Sheath 32 is hollow and receives a movable member or snare wire 34, the diameter of snare wire 34 being sufficiently small that it is freely slidable longitudinally of sheath 32. A snare loop 36 is formed at the distal end 38 of snare wire 34, loop 36 extending beyond the distal end 40 of sheath 32. The particular structure of snare loop 36 in the illustrated embodiment will be discussed subsequently.

The cannula operating handle or body 12 includes a generally right circular cylindrical inner wall 42 which slidingly engages the forward and rearward end walls 44, 46, respectively, of a slide 48. As best illustrated in FIG. 1, the walls 44, 46 are generally circular to the shape to conform to the cross section of inner wall 42 transversely of the longitudinal extent of handle or body 12. Slide 48 further includes a longitudinally extending channel 50 opening downwardly and provided at its vertically upper extent 52 with a plurality of teeth forming a rack 54. Rack 54 extends substantially the full length of slide 48 in the channel 50.

Body 12 is provided with a slot 56 (FIG. 2) through the side wall thereof. A first thumbwheel 58 is mounted upon an axle 60 for rotation in slot 56. The periphery of thumbwheel 58 is provided with a plurality of teeth 62 to form a pinion gear which engages rack 54. Manipulation of thumbwheel 58 causes slide 48 to slide longitudinally within body 12.

Forward and rearward end walls 44, 46 are provided with circular cross section aligned apertures 64, 66, respectively. An aperture 68, which is in alignment with apertures 64, 66 is provided in end cap 16. All of apertures 64, 66, 68 are also generally in alignment with aperture 24 in nut 22. A stem 70, which is generally circular in cross section and provided with diametrically opposed, longitudinally extending flats 72 is received in apertures 64, 66, 68. Stem 70 is provided with a reduced diameter circular cross section portion 74. Rearward wall 46 of slide 48 is provided with a slot 76 in the vertically upper portion thereof, the slot 76 extending generally parallel to the axially facing surfaces 78, 80 of wall 46. A somewhat C-shaped keeper 82 is positioned in slot 76, the keeper engaging the reduced diameter portion 74 of stem 70 to position stem 70 longitudinally with respect to slide 48, while at the same time permitting rotation of stem 70 about its axis within apertures 64, 66. A second thumbwheel 84 having a generally circular aperture 86 (FIG. 1) with flats 88 on both sides thereof is longitudinally slidably mounted on stem 70. Flats 88 engage flats 72 on the stem, such that rotation of thumbwheel 84 causes rotation of stem 70. Thumbwheel 84 is positioned between walls 44, 46 and is accessible through a peripherally extending slot 90 in the wall 42 of body 12 for manipulation to rotate stem 70.

The distal end 92 of stem 70 receives the proximal end 94 of snare wire 34. Proximal end 94 of snare wire 34 extends through stem 70 to near the proximal end 96 thereof. Proximal end 94 of snare wire 34 is held in place in stem 70 by a set screw 93 which is inserted through a threaded bore 95 in the stem 70 side wall. Movement of the stem 70 is transmitted to snare wire 34, and through snare wire 34 to the snare loop 36. Typically, snare wire 34 and loop 36 will be constructed from electrically conductive materials, with the sheath 32 constructed from an insulative material. Generally, of course, wire 34 and sheath 32 are fairly flexible to pass with little difficulty and without resulting injury through, for example, the gastrointestinal tract of a person upon whom a polypectomy procedure is to be performed. The proximal end 96 of stem 70 is provided with a terminal or socket 98 adapted to receive a male plug 100 (FIG. 1) of an RF generator (not shown). Radio frequency energy supplied from the generator through plug 100, socket 98, and intermediate conductor (not shown) which extends longitudinally within stem 70, and snare wire 34 to loop 36, is used to cauterize the area resulting from removal of a polyp or other obstruction which is removed from for example, the gastro-intestinal tract.

The polypectomy apparatus 10 structure thus far described provides significant advantages over such prior art structures as, for example, the structure of U.S. Pat. No. 3,955,578 in that the snare operating handle construction permits one-handed operation of the polypectomy apparatus, both for snare protraction and retraction and for snare rotation, by a surgeon. This is important as well as convenient for the surgeon since, in a typical application, the surgeon will be operating a light source for illuminating the surgery side, observing the surgical procedure, e.g., by means of an optical waveguide, and operating a polyp retriever, concurrently with the operation of the snare.

Attention is now drawn to the configuration of the snare loop 36 itself. It may be seen that, unlike known prior art loops, snare loop 36 is not generally flat and planar. Rather, each side of snare loop 36 is bent, as best illustrated in FIG. 3, into a somewhat W-shaped configuration. Generally, each side 102, 104 of loop 36 is bent at 106, 108, 110 into this "double-bent" configuration.

As can be seen from FIG. 3, a view taken generally in a first plane which extends longitudinally of the cannula across the loop 36 and FIG. 4, a view taken generally in a plane which is perpendicular to the first plane and parallel to the longitudinal extent of the cannula, partial retraction of the loop 36 into the distal end 40 of sheath 32 (such partial retraction being across the bend 106 but not across the bend 108 in each of sides 102, 104 of loop 36) causes the loop 36 to move parallel to the first plane and perpendicular to the second plane in somewhat of a "flipping" motion. This flipping of the loop 36 within, for example, the intestine of a surgical patient can be used to advantage by the surgeon operating apparatus 10 to ensnare a polyp for removal. The position of loop 36 after flipping is illustrated in broken lines in FIG. 1. This feature aids substantially the utility of the loop 36.

Figure 6:
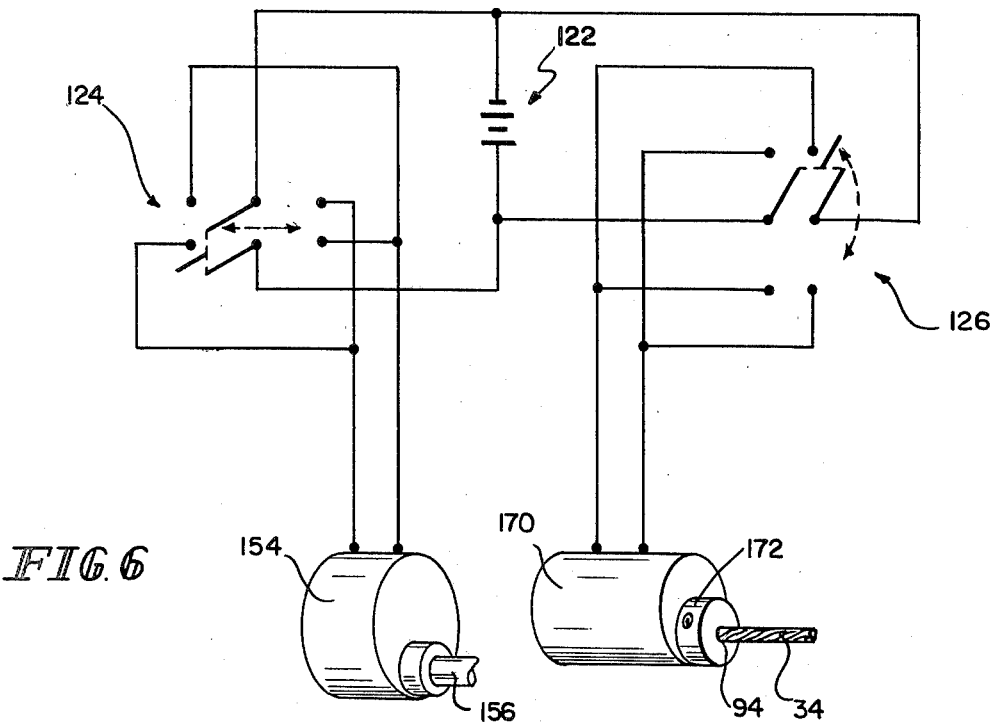

Turning now to the embodiment of the invention illustrated in FIGS. 5–6, those elements numbered identically with the elements in the embodiment of FIGS. 1–2 perform the same or similar functions. The apparatus 10' of FIG. 5 includes the cannula operating handle or body 12 having a proximal end 14 covered by end cap 16 and a distal end 18. The proximal end 30 of the cannula sheath 32 is attached to the distal end 18 in the same manner as in the embodiment of FIGS. 1-2, i.e., through a threaded aperture 20, a nut 22 having an aperture 24, and a collar 26.

The cannula operating handle 12 includes an inner proximal or rearward end portion 120 housing a suitable power source, in this embodiment, a pair of dry cells 122. Dry cells 122 are coupled through suitable electrical conductors to a double-pole double-throw, protract/retract electrical switch 124 and a similar double-pole double-throw, rotate right/rotate left switch 126. Each of switches 124, 126 includes an operating lever 128, 130, respectively. Switches 124, 126 are housed within the generally right circular cylindrical body 12 adjacent a thumb control opening 132 through the cylindrical wall 42 of body 12. Body 12 is further provided with an interior generally cylindrical wall 134 which extends part way around the inner periphery of body 12 and includes a longitudinally extending slot 136 adjacent the rearward or proximal end 138 of thumb control opening 132, and a peripherally extending slot 140 adjacent the forward or distal end 18 of body 12. A thumb control 142 having a thumb engaging portion 144 projecting above the cylindrical side wall of body 12, and a part-cylindrical portion or skirt 146 is mounted in the body 12. The thumb engaging portion 144 projects through the thumb control opening 132 for access by an operator, and the skirt 146 is freely slidably received within the space 148 defined between outer cylindrical wall 42 and the inner part-cylindrical wall 134. The skirt 146 of control 142 includes a peripherally extending slot 150 which receives the operating lever 128 of the protract/retract switch 124, and a longitudinally extending slot 152 which receives the operating lever 130 of the rotate right/rotate left switch 126.

Switch 124 is coupled by suitable electrical conductors to the terminals of a protract/retract motor-transmission 154 which includes a reversible DC motor. The output shaft 156 of motor-transmission 154 is coupled to a worm 158 which is suitably journalled for rotation at its forward end 160 within body 12. A carrier 162 is mounted upon worm 158, the carrier 162 including a follower 164 which advances the entire carrier 162 toward the distal end of body 12 as the worm 158 is rotated in one direction and retracts the carrier 162 from the distal end of body 12 as worm 158 is rotated in the opposite direction, the carrier 162 being slidably mounted within the generally cylindrical side wall 42 of body 12.

Rotate right/rotate left switch 126 is coupled through suitable conductors to a rotate right/rotate left motor-transmission 170 which is mounted upon carrier 162 for movement therewith. The conductors coupling motor-transmission 170 to switch 126 permit such movement of the motor-transmission 170. The proximal end 94 of snare wire 34 is coupled directly to the output shaft 172 of the rotate right/rotate left motor-transmission 170.

In operation, the thumb control 142 of the embodiment of FIGS. 5-6 is permitted to slide forwardly and rearwardly longitudinally of housing 12 without damaging operating lever 130 by the longitudinally extending slot 152 in skirt 146. The engagement of operating lever 128 in the peripherally extending slot 150 of skirt 146 causes actuation of the protract/retract switch 124 and motor-transmission 154 to protract the snare 36 from the distal end 38 of sheath 32. Movement of thumb control 142 longitudinally rearwardly (toward the proximal end) of body 12 actuates the protract/retract switch 124 to reverse the polarity of the dry cells 122 across the motor in motor-transmission 154, retracting snare 36 into the distal end 38 of sheath 32.

Movement of thumb control 142 peripherally along the side wall 42 of body 12 is permitted without damage to operating lever 128 of switch 124 by the engagement of lever 128 in the peripherally extending slot 150 of skirt 146. Such peripheral movement of thumb control 142 to the left (counterclockwise about body 12 when viewed from the proximal end 14 thereof) moves operating lever 130 of rotate right/rotate left switch 126 toward the left, coupling the dry cells 122 in a first polarity across the motor of rotate right/rotate left motor-transmission 170, causing rotation of the snare wire 34 toward the left. Movement of the thumb control 142 toward the right (clockwise when viewed from the proximal end 14 of body 12) moves operating lever 130 toward the right, actuating switch 126 to reverse the polarity of cells 122 across the motor in motor-transmission 170, rotating the snare wire 34 and snare loop 36 toward the right. The neutral positions of operating levers 128, 130 disconnect dry cells 122 from both of motor-transmissions 154, 170.

What is claimed is:

1. In a surgical apparatus including a sheath having proximal and distal ends, a snare wire extending within the apparatus and having proximal and distal ends, a loop formed at the distal end of the snare wire, and means for protracting the distal end of the snare wire including the loop from, and retracting the distal end of the snare wire including the loop into, the distal end of the sheath, the loop being formed with a double offset bend in a plane extending longitudinally of the cannula through the loop, such that partial retraction of the loop into the distal end of the sheath causes the loop to move parallel to the first plane and perpendicular to a second plane which is perpendicular to the first plane and parallel to the longitudinal extent of the cannula.

2. The apparatus of claim 1 wherein the loop is somewhat W-shaped in the plane extending longitudinally of the cannula through the loop.

3. For use with a surgical apparatus including a sheath having proximal and distal ends, a movable member disposed within the sheath and movable longitudinally therein, the movable element having proximal and distal ends, and a surgical instrument operable by movement of the distal end of the movable member with respect to the distal end of the sheath, an operating assembly comprising a body shaped to provide a hand grip and a body interior, a slide slidably received in the body interior and a stem rotatably mounted on the slide for movement longitudinally with the slide, first rotary means for engaging the slide and second rotary means for engaging the stem, the body including a distal end for fixed attachment of the proximal end of the sheath thereto, the distal end of the body defining an aperture through which the proximal end of the movable member movably extends, the proximal end of the movable member being coupled to the stem, the first rotary means being selectively rotatable to move the slide, and thus the movable member, longitudinally of the sheath, and the second rotary means being selectively rotatable to rotate the stem, and thus the movable member, with respect to the sheath.

4. The apparatus of claim 3 wherein the proximal end of the stem includes means defining a terminal for attachment to a source of electrical energy and a conductor providing electrical contact between the terminal and the proximal end of the movable member, the movable member including an electrically conductive portion.

5. The apparatus of claim 3 wherein the body includes means defining a generally cylindrical interior and the slide includes means providing a pair of walls spaced apart longitudinally of the cylinder axis and shaped to slide in the cylinder.

6. The apparatus of claim 5 wherein the walls have substantially the same shape as the body interior wall.

7. An apparatus including a flexible sheath having proximal and distal ends, a flexible member disposed within the sheath and movable longitudinally therein, the movable member having proximal and distal ends, and a surgical instrument operable by movement of the distal end of the movable member with respect to the distal end of the sheath, an operating assembly comprising first means for moving the movable member longitudinally with respect to the sheath, second means for rotating the movable member within the sheath, and a body for supporting the first and second means, the body including a distal end for fixed attachment of the proximal end of the sheath thereto, the distal end of the body further defining an aperture through which the proximal end of the movable member movably extends, the proximal end of the movable member being coupled to the first and second means for movement thereby, the first means including a slide supported in the body for movement longitudinally thereof, the body including means defining a generally cylindrical interior wall and the slide including means providing a pair of walls spaced apart longitudinally of the cylinder axis and shaped to slide in the cylinder, the second means comprising a stem rotatably mounted with respect to the first means, the stem having proximal and distal ends, the proximal end of the movable member being fixedly attached to the distal end of the stem.

8. The apparatus of claim 7 wherein the stem includes a thumbwheel for manipulation to rotate the stem with respect to the first means, the thumbwheel being accessible through the body.

9. The apparatus of claim 8 wherein the thumbwheel is axially slidably mounted on the stem.

10. An apparatus including a flexible sheath having proximal and distal ends, a flexible member disposed within the sheath and movable longitudinally therein, the movable member having proximal and distal ends, and a surgical instrument operable by movement of the distal end of the movable member with respect to the distal end of the sheath, an operating assembly comprising first means for moving the movable member longitudinally with respect to the sheath, second means for rotating the movable member within the sheath, and a body for supporting the first and second means, the body including a distal end for fixed attachment of the proximal end of the sheath thereto, the distal end of the body further defining an aperture through which the proximal end of the movable member movably extends, the proximal end of the movable member being coupled to the first and second means for movement thereby, the first means including a carriage supported in the body for movement longitudinally thereof, the body including means defining a generally cylindrical interior wall and the carriage including means shaped to slide in the cylinder, the second means comprising a stem rotatably mounted with respect to the first means, the stem having proximal and distal ends, the proximal end of the movable member being fixedly attached to the distal end of the stem.

11. The apparatus of claim 10 wherein the stem includes a thumbwheel for manipulation to rotate the stem with respect to the first means, the thumbwheel being accessible through the body.

12. The apparatus of claim 11 wherein the proximal end of the stem includes means defining a terminal for attachment to a source of electrical energy, the stem further including means providing electrical contact between the terminal and the proximal end of the movable member, the movable member also being conductive.

13. The apparatus of claim 11 wherein the thumb wheel is axially slidably mounted on the stem.

14. For use in operating a surgical cannula including a sheath and a snare provided at its distal end with a loop adapted for withdrawal into the sheath, an operating handle comprising a stem for attaching to the proximal end of the snare, a slide for rotatably supporting the stem and a body for slidably supporting the slide, the slide being slidable longitudinally within the body, the slide including means defining a rack and the body including means providing a combination thumbwheel and pinion gear engaging the rack, the pinion gear being accessible through the body for rotation to move the rack to project the loop from, and retract the loop into, the end of the sheath, respectively.

15. The apparatus of claim 14 wherein the stem includes means defining a thumbwheel freely movable longitudinally of the stem and fixed for rotation with the stem, the thumbwheel being accessible without the body, rotation of the thumbwheel causing rotation of the stem and rotation of the loop about the axis of the distal end of the snare within the sheath.

16. For use with a surgical apparatus including a sheath having proximal and distal ends, a movable member disposed within the sheath and movable longitudinally therein, the movable member having proximal and distal ends, and a surgical instrument operable by movement of the distal end of the movable member with respect to the distal end of the sheath, an operating assembly comprising a body shaped to provide a hand grip and a body interior, a slide slidably received in the body interior and a stem rotatably mounted on the slide for movement longitudinally with the slide, first rotary means for engaging the slide and second rotary means for engaging the stem, the body including a distal end for fixed attachment of the proximal end of the sheath thereto, the distal end of the body defining an aperture through which the proximal end of the movable member movably extends, the proximal end of the movable member being coupled to the stem, the first rotary means being selectively rotatable to move the slide, and thus the movable member, longitudinally of the sheath, and the second rotary means being selectively rotatable to rotate the stem, and thus the movable member, with respect to the sheath, the slide comprising a portion defining a rack and the first rotary means including a first thumbwheel rotatably mounted in, and accessible through, the body, the periphery of the first thumbwheel providing pinion gear teeth to engage the rack, manipulation of the first thumbwheel causing movement of the slide.

17. The apparatus of claim 16 wherein the second rotary means includes a second thumbwheel longitudinally slidably mounted on, and fixed for rotation with the stem for manipulation to rotate the stem with respect to the slide, the second thumbwheel being accessible through the body.

18. An apparatus including a sheath having proximal and distal ends, a member disposed within the sheath and movable longitudinally therein, the movable member having proximal and distal ends, and a surgical instrument operable by movement of the distal end of the movable member with respect to the distal end of the sheath, an operating assembly comprising first means for moving the movable member longitudinally with respect to the sheath, second means for rotating the movable member within the sheath, and a body for supporting the first and second means, the body including a distal end for fixed attachment of the proximal end of the sheath thereto, the distal end of the body further defining an aperture through which the proximal end of the movable member movably extends, the proximal end of the movable member being coupled to the first and second means for movement thereby, the first means including a carriage supported in the body for movement longitudinally thereof, the body including means defining a generally cylindrical interior wall and the carriage including means shaped to slide in the cylinder, the carriage comprising a portion defining a rack, the first means further including a first thumbwheel rotatably mounted in the body, the periphery of the first thumbwheel providing pinion gear teeth to engage the rack, manipulation of the first thumbwheel causing movement of the carriage.

19. An apparatus including a sheath having proximal and distal ends, a member disposed within the sheath and movable longitudinally therein, the movable member having proximal and distal ends, and a surgical instrument operable by movement of the distal end of the movable member with respect to the distal end of the sheath, an operating assembly comprising first means for moving the movable member longitudinally with respect to the sheath, second means for rotating the movable member within the sheath, and a body for providing a hand grip and for supporting the first and second means, the body including a distal end for fixed attachment of the proximal end of the sheath thereto, the distal end of the body further defining an aperture through which the proximal end of the movable member movably extends, the proximal end of the movable member being coupled to the first and second means for movement thereby, the first means including a slide supported in the body for movement longitudinally thereof, the body including means defining a generally cylindrical interior wall and the slide including means shaped to slide in the cylinder, the slide comprising a portion defining a rack, the first means further including a first thumbwheel rotatably mounted in the body, the periphery of the first thumbwheel providing pinion gear teeth to engage the rack, manipulation of the first thumbwheel causing movement of the slide, the second means comprising a stem rotatably mounted with respect to the first means, the stem having proximal and distal ends, the proximal end of the movable member being fixedly attached to the distal end of the stem, and a second thumbwheel movably mounted on the stem for manipulation to rotate the stem with respect to the first means, the first and second thumbwheels being accessible through the body.

20. The apparatus of claim 19 wherein the proximal end of the stem includes means defining a terminal for attachment to a source of electrical energy, the stem further including means providing electrical contact between the terminal and the proximal end of the movable member, the movable member also being conductive.

21. An apparatus including a sheath having proximal and distal ends, a member disposed within the sheath and movable longitudinally therein, the movable member having proximal and distal ends, and a surgical instrument operable by movement of the distal end of the movable member with respect to the distal end of the sheath, an operating assembly comprising first means for moving the movable member longitudinally with respect to the sheath, second means for rotating the movable member within the sheath, and a body for supporting the first and second means, the body including a distal end for fixed attachment of the proximal end of the sheath thereto, the distal end of the body further defining an aperture through which the proximal end of the movable member movably extends, the proximal end of the movable member being coupled to the first and second means for movement thereby, the first means including a carriage supported in the body for movement longitudinally thereof, the body including means defining an interior and the carriage including means shaped to slide in the body interior, the carriage including a portion defining a worm follower, and the first means including a worm supported for rotation in the body and engaged by the follower.

22. The apparatus of claim 21 and further comprising an electric motor, the work being coupled to the motor for rotation thereby to drive the carriage longitudinally of the body.

* * * * *

UNITED STATES PATENT AND TRADEMARK OFFICE
CERTIFICATE OF CORRECTION

PATENT NO. : 4,256,113
DATED : March 17, 1981
INVENTOR(S) : Dale L. Chamness

It is certified that error appears in the above-identified patent and that said Letters Patent are hereby corrected as shown below:

Column 1, line 6, change "tion" to --ting--.

Column 6, line 49, change "element" to --member--.

Column 10, line 49, change "work" to --worm--.

Signed and Sealed this

Eleventh Day of August 1981

[SEAL]

Attest:

Attesting Officer

GERALD J. MOSSINGHOFF
Commissioner of Patents and Trademarks